United States Patent
Govari et al.

(10) Patent No.: US 9,474,466 B2
(45) Date of Patent: Oct. 25, 2016

(54) LOW-PROFILE LOCATION PAD FOR MAGNETIC-BASED INTRA-BODY PROBE TRACKING SYSTEM

(71) Applicant: BIOSENSE WEBSTER (ISRAEL) LTD., Yokneam (IL)

(72) Inventors: Assaf Govari, Haifa (IL); Yaron Ephrath, Karkur (IL); Andres Claudio Altmann, Haifa (IL); Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 100 days.

(21) Appl. No.: 14/138,654

(22) Filed: Dec. 23, 2013

(65) Prior Publication Data
US 2015/0173643 A1    Jun. 25, 2015

(51) Int. Cl.
A61B 5/05    (2006.01)
A61B 5/06    (2006.01)

(52) U.S. Cl.
CPC .............. *A61B 5/065* (2013.01); *A61B 5/062* (2013.01); *Y10T 29/4902* (2015.01)

(58) Field of Classification Search
USPC ........................................................ 600/424
See application file for complete search history.

(56) References Cited

U.S. PATENT DOCUMENTS

| 5,239,489 | A | * | 8/1993 | Russell | G06F 3/046 |
| | | | | | 178/18.07 |
| 2006/0241397 | A1 | * | 10/2006 | Govari et al. | 600/424 |
| 2007/0265526 | A1 | | 11/2007 | Govari et al. | |
| 2008/0231263 | A1 | * | 9/2008 | Rebmann | G01D 5/142 |
| | | | | | 324/207.11 |
| 2009/0082989 | A1 | | 3/2009 | Zuhars | |
| 2010/0234724 | A1 | * | 9/2010 | Jacobsen et al. | 600/424 |
| 2013/0072774 | A1 | | 3/2013 | Greenspan | |

FOREIGN PATENT DOCUMENTS

| EP | 1 854 405 A1 | 11/2007 |
| EP | 2 546 671 A1 | 1/2013 |
| WO | WO 2013/142386 A1 | 9/2013 |

OTHER PUBLICATIONS

EP Search Report, EP Application 14 19 9754 Dated Apr. 15, 2015.

* cited by examiner

*Primary Examiner* — Joel F Brutus
(74) *Attorney, Agent, or Firm* — Notaro, Michalos & Zaccaria P.C.

(57) ABSTRACT

A location pad includes a housing having a flat surface and multiple field generators. The multiple field generators are fixed to the housing and are configured to generate respective magnetic fields having respective axes that are perpendicular to the flat surface.

20 Claims, 4 Drawing Sheets

LOW-PROFILE LOCATION PAD FOR MAGNETIC-BASED INTRA-BODY PROBE TRACKING SYSTEM

FIELD OF THE INVENTION

The present invention relates generally to intra-body position tracking, and particularly to magnetic-based position tracking of intra-body probes.

BACKGROUND OF THE INVENTION

The position of an intra-body probe, such as a catheter, can be tracked in the body of a patient using magnetic position tracking techniques. For example, U.S. Patent Application 2007/0265526, whose disclosure is incorporated herein by reference, describes a magnetic position tracking system for performing a medical procedure on a patient. The patient is positioned on an upper surface of a table includes a location pad, which is positioned on the upper surface of the table beneath the patient. The location pad includes one or more field generators, which are operative to generate respective magnetic fields and are arranged so that a thickness dimension of the location pad is no greater than 3 centimeters. A position sensor is fixed to an invasive medical device for insertion into a body of the patient, and is arranged to sense the magnetic fields so as to measure a position of the medical device in the body.

Magnetic resonance imaging (MRI) is an imaging technique used for visualizing tissue, particularly soft tissue, of a patient. The technique relies on exciting nuclei, typically hydrogen nuclei, from their equilibrium state, and measuring the resonant radio-frequency signals emitted by the nuclei as they relax back to equilibrium. The measured resonant radio-frequency signals are used to create high quality images of the tissue. Medical practitioners may use MRI in conjunction with other medical procedures.

SUMMARY OF THE INVENTION

An embodiment of the present invention provides a location pad including a housing having a flat surface and multiple field generators. The multiple field generators are fixed to the housing and are configured to generate respective magnetic fields having respective axes that are perpendicular to the flat surface.

In some embodiments, the flat surface lies in a plane. In other embodiments, the flat surface is curved. In yet other embodiments, the housing has a thickness no greater than 5 millimeters. In some embodiments, the field generators include coils having windings that are parallel to the surface. In other embodiments, the housing includes elastic material that is configured to hold the field generators and to dampen resonances in the field generators.

There is also provided, in accordance with an embodiment of the present invention, a method for producing a location pad, including providing a housing having a flat surface. Multiple field generators are fixed to the housing, such that the field generators generate respective magnetic fields having respective axes that are perpendicular to the flat surface.

There is additionally provided, in accordance with an embodiment of the present invention, a method for position tracking including driving multiple field generators that are coupled to a flat surface in a vicinity of a patient body with multiple respective drive signals, so as to cause the field generators to generate respective magnetic fields having respective axes that are perpendicular to the flat surface. At least one electrical signal is measured that is induced by the magnetic fields in a position sensor coupled to an intra-body probe inserted into the patient body. A position of the probe in the body is estimated based on the electrical signal.

In some embodiments, the position sensor includes a single-axis sensor. In other embodiments, estimating the position of the probe includes computing an average magnitude of the electrical signal, and estimating a distance of the probe from the flat surface depending on the average magnitude.

In some embodiments, estimating the position of the probe includes computing magnitudes of multiple components of the electrical signal induced respectively by the magnetic fields generated by the multiple field generators, and estimating a lateral position of the probe relative to the field generators depending on the average magnitude. In other embodiments, driving the field generators includes generating the multiple drive signals having different respective frequencies, and computing the magnitudes includes distinguishing among the components of the electrical signal by discriminating among the different frequencies. In yet other embodiments, estimating the position of the probe includes refining the position of the probe by performing an iterative position estimation process that uses at least the lateral position as an initial condition.

The present invention will be more fully understood from the following detailed description of the embodiments thereof, taken together with the drawings in which:

DETAILED DESCRIPTION OF EMBODIMENTS

Overview

Intra-body probes, such as catheters, are used in various therapeutic and diagnostic medical procedures. The probe is inserted into the living body of a patient and navigated to the target region in a body cavity to perform the medical procedure. In magnetic field-based position tracking systems, an external magnetic field is applied to the patient's body. A sensor installed near the distal end of the catheter responds to the field by producing an electric signal. The signal is used by the tracking system to locate the position and orientation of the catheter in the patient's body. The magnetic field is typically produced by multiple field generators, e.g., field-generating coils.

Embodiments of the present invention that are described herein provide small and flat location pad configurations. The disclosed location pads comprise multiple magnetic field generators (e.g., planar coils) that are mounted on a surface. The axes of the field generators are all perpendicular to the surface. When the surface is entirely flat, the axes of the field generators are parallel to one another.

The resulting location pad has a low profile, and can be easily placed under the patient. In some embodiments, the location pad surface is slightly shaped, i.e., deviates slightly from a flat plane, for example in order to fit into an MRI scanner.

In some embodiments, the field generators in the location pad are driven with Alternating-Current (AC) drive signals having different frequencies, such that the signals induced in the sensor at the catheter distal end can be distinguished from one another. The use field generators having parallel axes facilitates the mathematical modeling of the resulting magnetic field, which simplifies the computation of the position and orientation of the distal end of the catheter based on the catheter sensor output.

In an example implementation, the probe position is estimated in a two-stage process. In the first stage, the height of the probe above the plane of the location pad is estimated from the absolute magnitude of the composite signal sensed by the position sensor in the probe. Then, the transverse position of the probe relative to the location pad can be determined by analyzing the relative amplitudes of the different frequencies in the composite signal. This initial estimate can be output per-se, or it can be used as the starting point to a more accurate, iterative position estimation process.

In some embodiments, the field generators comprise coils that are embedded in silicone within a housing, so as to dampen audio frequency resonance that may be generated by the MRI scanner. In other embodiments, electrical transformers are used for impedance matching between low impedance amplifiers used to drive signals into the high impedance magnetic coils.

In summary, the improved location pad configurations described herein permit operating a magnetic probe tracking system while the patient is within a second magnetic environment of an MRI scanner. The disclosed location pads are suitable for use with single-axis position sensors in the probe, such that simpler and thinner probes may be used in the medical procedure.

System Description

Figure 1:
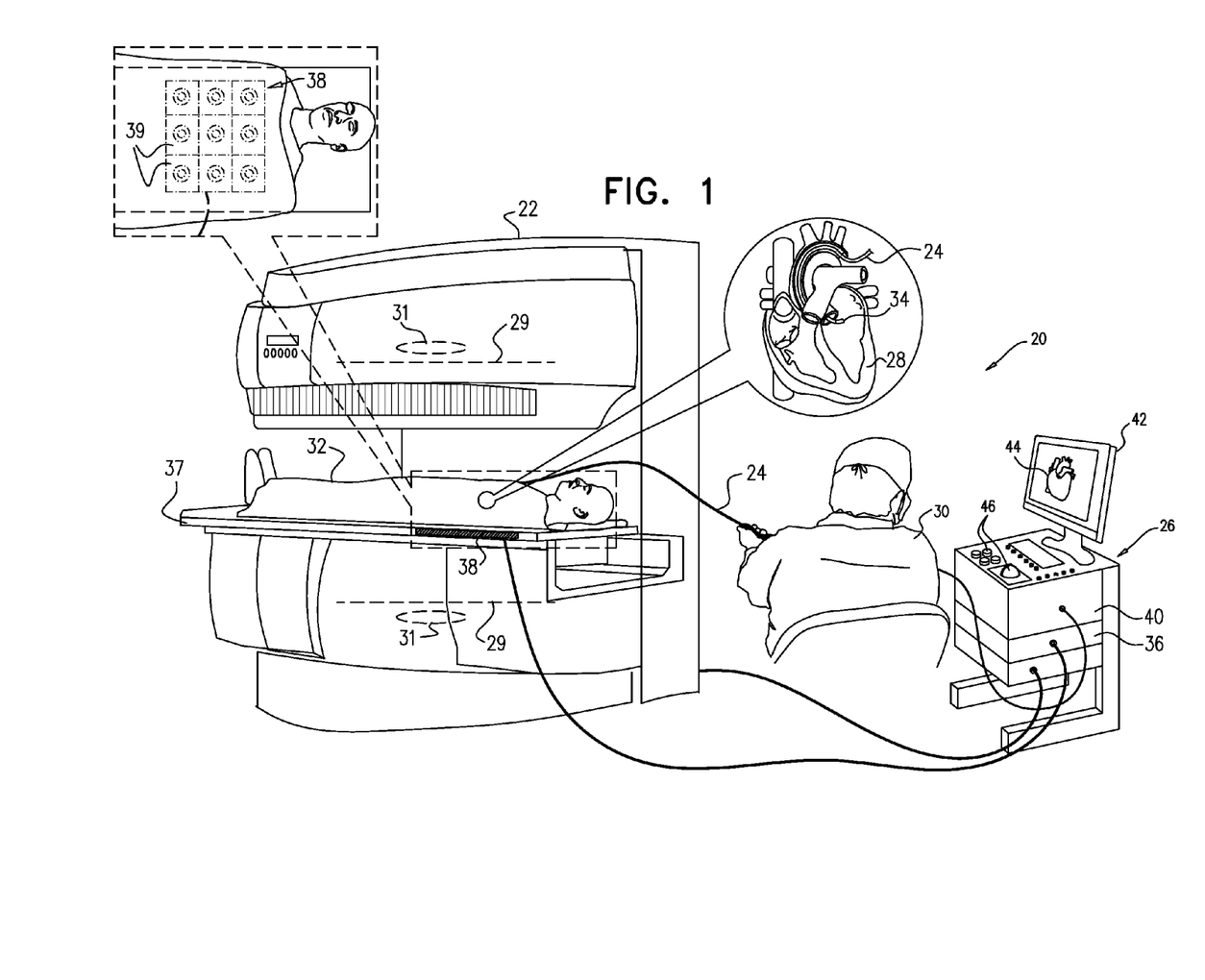
FIG. 1 is a schematic, pictorial illustration of a magnetic catheter tracking system collocated with a magnetic resonance imaging (MRI) system, in accordance with an embodiment of the present invention.

FIG. 1 is a schematic, pictorial illustration of a system 20 for magnetic catheter tracking collocated with magnetic resonance imaging (MRI), in accordance with an embodiment of the present invention. System 20 comprises an MRI scanner 22, an intra-body probe 24, such as a catheter, and a control console 26. Probe 24 comprises a sensor at a distal end 34 of catheter 24 (as will be shown later in FIG. 2A), which is used for tracking the position of catheter 24 in the body of a patient 32.

Catheter 24 may be used, for example, for mapping electrical potentials in a chamber of a heart 28 of patient 32 with multiple electrodes disposed near distal end 34 of catheter 24 that contact the tissue of the heart cavity at multiple points. In alternative embodiments, catheter 24 may be used, mutatis mutandis, for other therapeutic and/or diagnostic functions in the heart or other body organs.

An operator 30, such as a cardiologist, percutaneously inserts probe 24 through the vascular system of patient 32 so that distal end 34 of the probe enters a body cavity, herein assumed to be the cardiac chamber. Distal end 34 is illustrated and explained in more detail with respect to FIG. 2A.

Console 26 uses magnetic position sensing to determine the orientation and position coordinates of distal end 34 of catheter 24 inside heart 28. For the sensing, console 26 operates a driver circuit 36 that drives one or more magnetic field generators 39 in a location pad 38 as shown in the inset, and below in cross-section below the patient's torso on a table 37. A position sensor installed in distal end 34 generates electrical signals in response to the magnetic fields generated by location pad 38, thereby enabling console 26 to determine the position and orientation of distal end 34 with respect to location pad 38, and thus, the position and orientation within the heart of patient 32.

MRI scanner 22 comprises magnetic field coils 29, including field gradient coils, which together generate a spatially variant magnetic field. The spatially variant magnetic field provides spatial localization for radio frequency (RF) signals generated by the scanner. In addition, the scanner comprises transmit/receive coils 31. In a transmit mode, coils 31 radiate RF energy to patient 32, the RF energy interacting with the nuclear spins of the patient's tissue and thereby realigning the magnetic moments of the nuclei away from their equilibrium positions. In a receive mode, coils 31 detect RF signals received from the patient's tissue as the tissue nuclei relax to their equilibrium state.

A processor 40 has dual functionality in the embodiment shown in FIG. 1. First, processor 40 has interface circuitry (not shown) to receive electrical signals induced in the sensor at catheter distal end 34 in response to the magnetic field generated by location pad 38, and uses the received electrical signal to locate the catheter in the patient's body.

Secondly, processor 40 operates MRI scanner 22 by using circuitry to control MRI coils 29, including forming required magnetic field gradients, as well as other circuitry to operate transmit/receive coils 31 around patient 32. Processor 40 acquires MRI data of heart 28 of patient 32, or at least of the cardiac chamber to be imaged, using signals received by coils 31. Using the data, processor 40 displays an image 44 of heart 28 to operator 30 on a display 42. Alternatively, the functions of processor 40 may be split between two processors, one managing the magnetic position tracking system and one managing the MRI scanner.

In some embodiments, the position of the catheter acquired by the magnetic tracking system can be superimposed on image 44 of heart 28 on display 42 acquired by MRI scanner 22. In yet other embodiments, operator 30 can manipulate image 44 using one or more input devices 46.

Processor 40 may also be configured to reduce any magnetic interference, or coexistence effects of the respective MRI system and magnetic catheter tracking systems, which may, for example, degrade system performance. Stated differently, processor 40 is configured to compensate for any coupling effects, for example, between the magnetic fields generated by MRI coils 29 and 31 used in MRI scanner 22, and the magnetic generators 39 in location pad 38 for the magnetic catheter tracking system.

Processor 40 typically comprises a general-purpose computer, which is programmed in software to carry out the functions that are described herein. The software may be downloaded to processor 40 in electronic form, over a network, for example, or it may be provided on non-transitory tangible media, such as optical, magnetic or electronic memory media. Alternatively, some or all of the functions of processor 40 may be carried out by dedicated or programmable digital hardware components, or by using a combination of hardware and software elements.

The magnetic catheter tracking system can be realized as the CARTO XP EP Navigation and Ablation System, available from Biosense Webster, Inc. (Diamond Bar, Calif.), suitably modified to execute the procedures described herein.

The embodiments shown in FIG. 1 are merely for conceptual clarity, and not by way of limitation of the embodiments of the present invention. MRI scanner 22 and the magnetic catheter tracking system may have separate processors for each system and not shared as in the embodiment shown in system 20. Single or separate displays may be used for the MRI scanner and the catheter tracking system.

MRI Compatible Location Pad

Figure 2A:
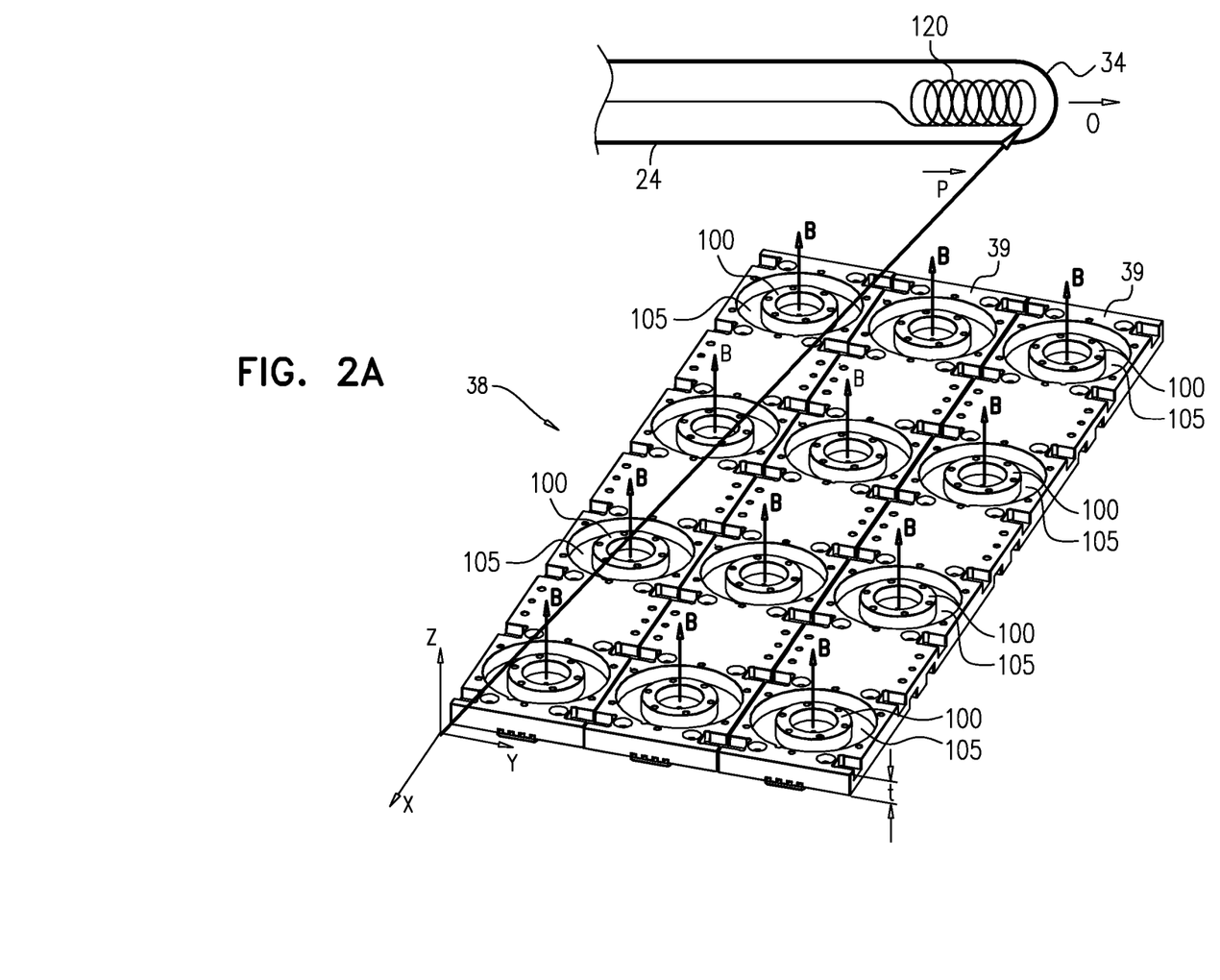
FIGS. 2A and 2B are schematic, pictorial illustrations of location pads, in accordance with embodiments of the present invention.

FIG. 2A is a schematic, pictorial illustration of location pad 38, in accordance with an embodiment of the present invention. Location pad 38 comprises multiple magnetic field generators 39 arranged in an array shown in the transverse XY plane of FIG. 2A. Twelve generators 39 of equal sizes are shown in the embodiment of FIG. 2A. The array is held in a housing which may be made from any suitable material, such as from various plastics. X-Y-Z coordinate axes are shown to the lower left side of the housing of location pad 39, which has a thickness t.

Each generator 39 comprises a planar coil 100 whose windings are parallel to the X-Y plane. In some embodiments, coil 100 is surrounded by a trench 105. The coil may be formed from any suitable material, such as copper. When a signal, typically a current, is applied to coil 100, coil 100 generates a magnetic field B oriented along the Z-axis in response to the applied signal and perpendicular to the plane of the coil (the X-Y plane). In this example, the axes of all the magnetic fields are parallel to one another and perpendicular to the surface of the location pad. The composite magnetic field in the region above the location pad comprises the superposition of magnetic fields B from the multiple field generators.

When patient 32 lies on location pad 38 as shown in the inset in FIG. 1 and catheter 24 is navigated into the target region within the patient's body above the location pad, a magnetic sensor coil 120 near distal end 34 of the catheter generates an electrical signal, typically a voltage, in response to the composite magnetic field. Sensor coil 120 is assumed here to be a single-axis sensor at distal end 34 of catheter 24. (Alternatively, catheter 24 may comprise a multiple-axis position sensor, e.g., a sensor comprising three mutually-orthogonal coils.)

In the embodiments presented herein, the location pad is configured to be placed between the patient and the top surface of table 37, e.g., with the patient lying on top of the location pad. The transverse dimensions of the location pad are typically confined to the transverse dimensions of patient table 37, which is moved into the MRI scanner. The thickness t of the location pad is usually configured to be no more than 5 mm. In this manner, the MRI scanner does not collide or interfere with location pad 38 of the magnetic tracking system, or vice versa.

Processor 40 in system 20 is configured to use the electrical signal sensed by sensor 120 to compute a position $\vec{P}$ vector and an orientation vector $\vec{O}$ of sensor 120 relative to the origin of the X-Y-Z axes. Position vector $\vec{P}$ is the vector from the origin to sensor 120. Orientation vector $\vec{O}$ is the axial vector through catheter 24. The position of the origin of the X-Y-Z coordinate system shown in FIG. 2A is merely for conceptual clarity, and not by way of limitation of the embodiments of the present invention. The origin may be defined in any suitable position relative to the location pad.

Figure 2B:
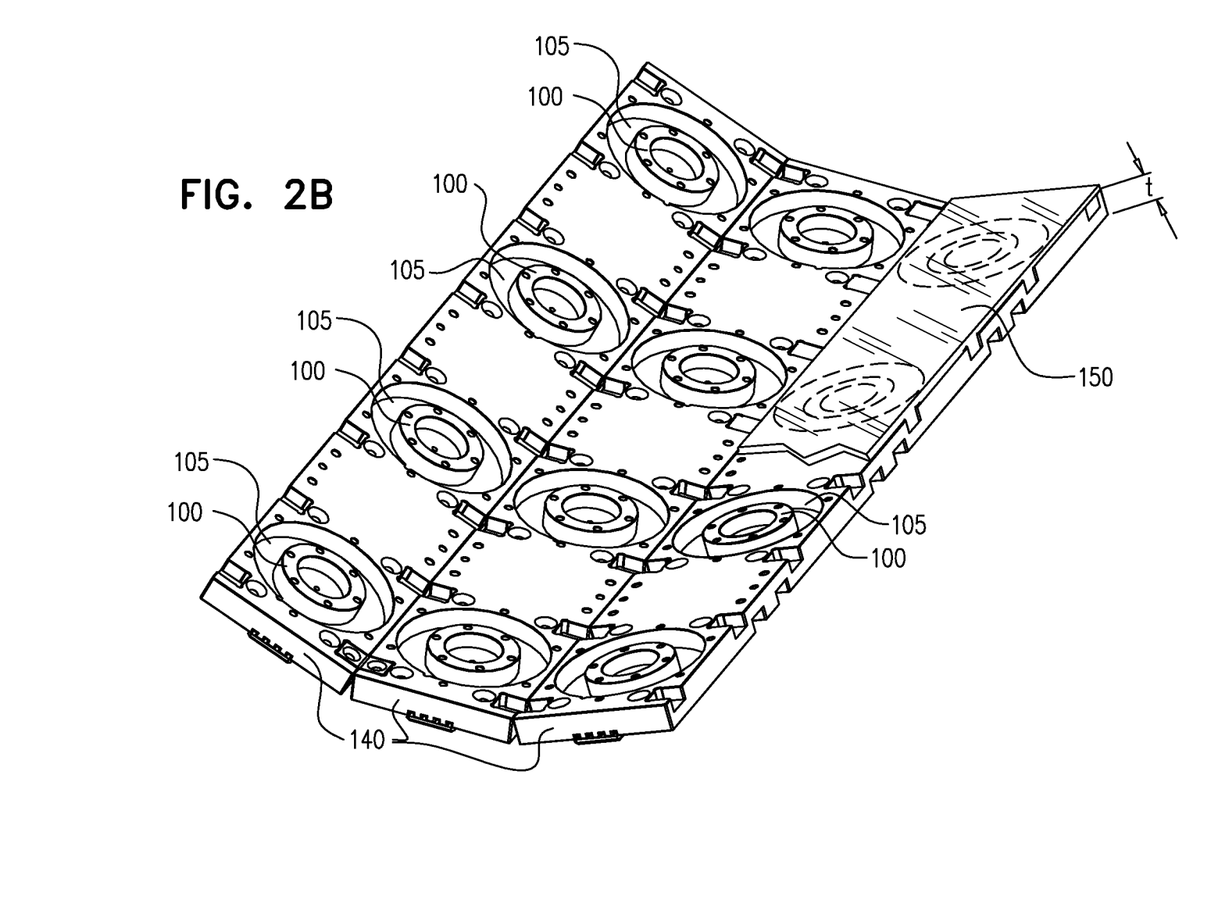

FIG. 2B is a schematic, pictorial illustration of an alternative embodiment of the location pad, in accordance with an embodiment of the present invention. In this embodiment, each row 140 of coils 100 is planar, but the rows lie on a slightly curved surface. In this configuration, too, the axes of the magnetic fields generated by coils 100 are perpendicular to the surface of the location pad. The curved configuration of FIG. 2B is useful, for example, for fitting into the chamber of MRI scanner 22.

On the right-most row shown in the FIG. 2B, magnetic field generators 39 have a lid 150 covering coils 100, which may be formed from any suitable material, such as a plastic, covering the entire array.

In the configuration of FIG. 2B, the magnetic fields B generated by coils 100 are nearly parallel to one another as will be described below. Any small deviations of the magnetic fields B from parallelism due to the curvature shown in FIG. 2B were found to have a negligible impact on the accuracy of the catheter position tracking system.

When location pad 38 is used in a MRI environment, the large magnetic MRI coils generate very large magnetic fields such as in the range of 0.5-3 Tesla. Magnetic catheter tracking systems, such as the CARTO system, use magnets with AC frequencies in the audio frequency range. Hence when magnetic coils 100 are driven with the audio frequencies in the presence of the large MRI magnets, small magnetic coils 100 can resonate at audio frequencies, e.g., from 19-22 kHz. Thus in some embodiments, the coils are potted in an elastic material, such as silicone or any other suitable material, in order to dampen or otherwise prevent this resonance. For example, trench 105 and any other regions around coil 100 can be filled with silicone, or any other suitable material, which dampen the audio frequency resonances of coils 100 in location pad 38 in an MRI environment.

Small magnetic coils 100 can also exhibit large impedances on the order of 600 ohms, e.g., due to skin effects at these frequencies as well as the small size of coils 100. These coils are driven with driver amplifier 36, which typically has an output characteristic impedance on the order of 6 ohms. In some embodiments, to drive these high impedance coils, transformers can be used in driver amplifier 36 with an impedance transformation ratio to overcome the impedance mismatches from 6 ohms to 600 ohms.

The array configurations of FIGS. 2A and 2B are shown merely for visual clarity and not by way of limitation of the embodiments of the present invention. Any suitable number of magnetic coils 100 in any suitable configuration may be used. Coils 100 are not limited to a flat circular shape, but may be of any suitable shape.

Computing the Position and Orientation of a
Catheter with the MRI Compatible Location Pad As explained above, in the disclosed embodiments the magnetic fields generated by coils 100 of location pad 38 are parallel to one another and perpendicular to the surface of the location pad. As a result, the magnitude of the composite magnetic field varies with the Z coordinate but is substantially constant as a function of X and Y. Therefore, when using a single-axis sensor (e.g., sensor 120 in FIG. 2A), the magnitude of the composite signal sensed by the sensor is strongly indicative of the height of distal end 34 above location pad 38, but is insensitive to the lateral position of the distal tip relative to the location pad. This insensitivity may cause inaccuracy or even lack of conversion in the position and orientation estimation process performed by processor 40.

One possible solution for this problem is to use a more complex position sensor in the catheter, such as a three-axis sensor. Such an arrangement is described in U.S. Patent Application Number US 2007/0265526, cited above. This solution, however, is complex and increases the catheter diameter.

In some embodiments, processor 40 estimates the position and orientation of catheter 24 is a two-stage process. This process, which is described below, enables the use of a single-axis sensor in conjunction with a low-profile location pad. The disclosed process is computationally-simple and converges quickly and efficiently. Typically, a total of five coils 100 is sufficient for providing accurate location, but a larger number of coils (e.g., twelve coils as shown in FIGS. 2A and 2B) is preferable for higher accuracy and robustness.

In some embodiments, coils 100 are driven with AC signals having different respective frequencies, so that the signals induced in the single axis sensor coil can be distinguished from one another.

Figure 3:
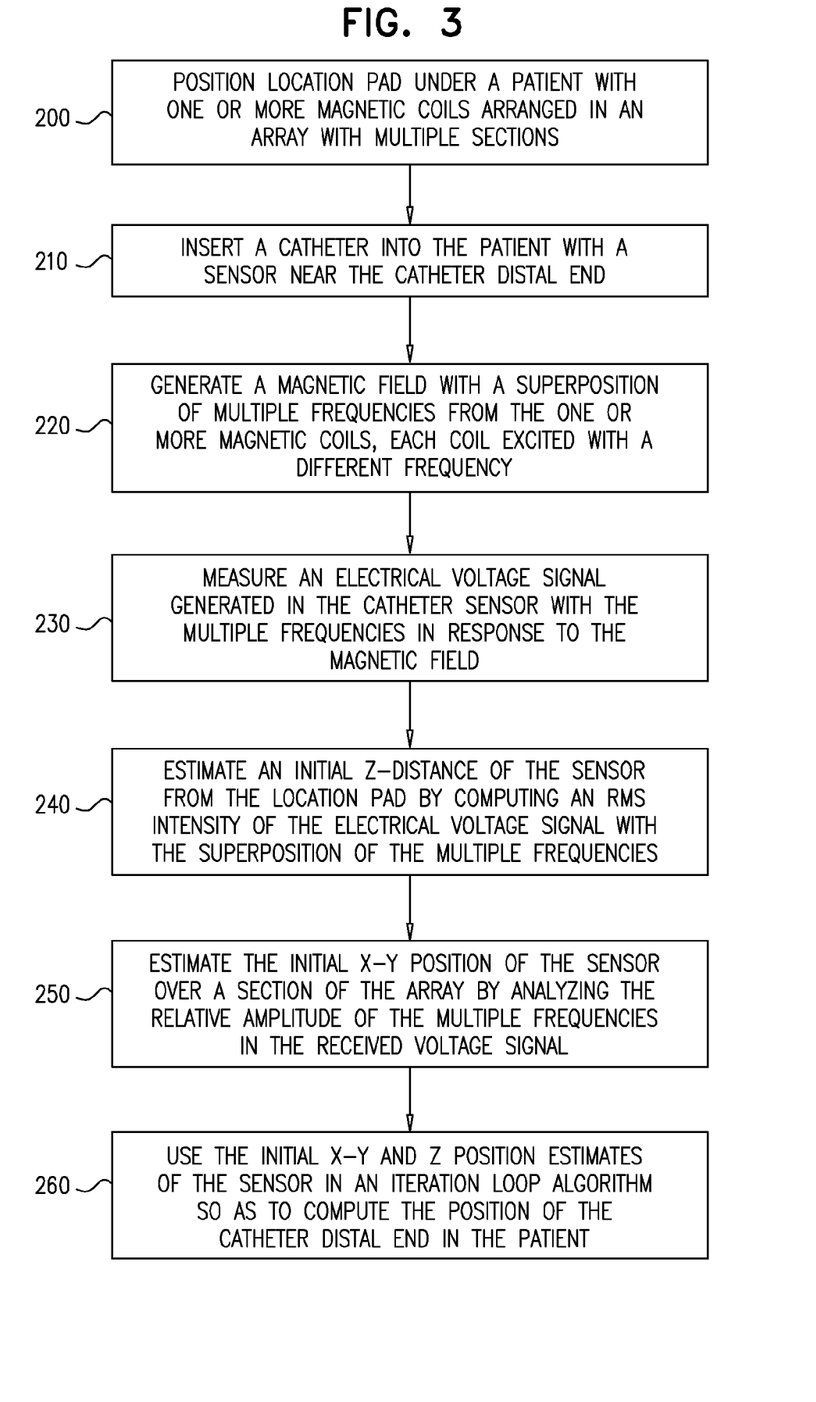
FIG. 3 is a flow chart that schematically illustrates a method for estimating the position of a catheter relative to a location pad, in accordance with an embodiment of the present invention.

FIG. 3 is a flow chart that schematically illustrates a method for estimating the position of distal end 34 of catheter 24 relative to location pad 38, in accordance with an embodiment of the present invention. In a positioning step 200, location pad 38 is positioned under patient 32. In an inserting step 210, catheter 24 is inserted into patient 32. In a generating step 220, coils 100 are driven with respective AC drive signals having different frequencies.

In measuring step 230, processor 40 measures the electrical voltage signal that is induced in catheter sensor 120 in response to the magnetic field. In a first estimating step 240, processor 40 estimates an initial Z-distance of the sensor from the location pad by computing the average (e.g., RMS) intensity of the electrical voltage signal (which is proportional to the average magnitude of the composite magnetic field produced by coils 100).

In a second estimating step 250, processor 40 estimates an initial X-Y position of the sensor relative to location pad 38, by analyzing the relative amplitudes of the individual different-frequency components in the induced voltage signal. Processor 40 is able to discriminate among the signal components induced by the different coils 100, because each signal component has a different frequency. Processor 40 may filter the signal sensed by sensor 120 with suitable digital filtering for this purpose.

In an iterative estimation step 260, processor 40 refines the initial X-Y position estimate from step 250 and Z position estimate from step 240 of the sensor. Typically, processor 40 carries out an iterative position estimation process that uses the initial X-Y-Z coordinate (output of steps 240 and 250) as initial conditions. Due to the relatively-accurate initial conditions, the iterative process converges quickly and reliably to the accurate X-Y-Z coordinate of the catheter distal end.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A location pad arrangement:
   the location pad arrangement comprising a location pad, a body probe, and a control console:
   wherein the location pad comprises a housing, the housing comprising at least one flat surface;
   the location pad further comprising at least five field generators fixed to the housing, the at least five field generators being configured to generate respective magnetic fields having respective axes that are perpendicular to the flat surface of the location pad;
   wherein a plurality of the at least five field generators are each individually surrounded by a respective concave trench, and wherein the trench is at least partially filled with elastic material, the elastic material therefore surrounding respective field generators, and being adapted to dampen frequency resonances;
   wherein the at least five field generators are spaced in two different dimensions with respect to the flat surface of the location pad such that the at least five field generators are not all arranged in a straight line;
   wherein the location pad comprises a plurality of substantially rigid, planar, parallel rows;
   wherein the at least five field generators are distributed among the plurality of rows, with at least some of the plurality of rows each holding a plurality of field generators;
   wherein the rows are capable of pivoting with respect to other adjacent rows such that the plurality of rows of the location pad can collectively form a concave surface;
   wherein the body probe is a tool for inserting into a patient, and comprises a position sensor, the position sensor being capable of generating electrical signals in response to magnetic fields generated by the at least five field generators; and
   wherein the control console is operatively linkable to the location pad and to the body probe, and is adapted to determine a position of the position sensor based on electrical signals received from the position sensor.

2. The location pad arrangement according to claim 1, wherein:
   said plurality of rows each have an elongated rectangular shape, each row comprising two longer sides and two shorter sides;
   said plurality of rows are positioned side-by-side so that a longer side of each row is adjacent a longer side of each adjacent row; and
   each row has a plurality of field generators positioned along its length.

3. The location pad arrangement according to claim 1, wherein a plurality of concave trenches are circular, and wherein the respective field generators are in the center of circular trenches.

4. The location pad arrangement according to claim 1, wherein the location pad housing has a thickness no greater than 5 millimeters.

5. The location pad arrangement according to claim 1, wherein the at least five field generators comprise coils having windings that are parallel to the surface.

6. A method for position tracking, comprising:
   providing a location pad arrangement according to claim 1;

driving multiple field generators that are coupled to a flat surface in a vicinity of a patient body with multiple respective drive signals, so as to cause the at least five field generators to generate respective magnetic fields having respective axes that are perpendicular to the flat surface;

measuring at least one electrical signal that is induced by the magnetic fields in the position sensor of the body probe while the body probe is inserted into the patient body; and estimating a position of the probe in the body based on the electrical signal.

7. The method according to claim 6, wherein estimating the position of the probe comprises computing an average magnitude of the electrical signal, and estimating a distance of the probe from the flat surface depending on the average magnitude.

8. The method according to claim 6, wherein estimating the position of the probe comprises computing magnitudes of multiple components of the electrical signal induced respectively by the magnetic fields generated by the multiple field generators, and estimating a lateral position of the probe relative to the at least five field generators depending on the average magnitude.

9. The method according to claim 8, wherein driving the at least five field generators comprises generating the multiple drive signals having different respective frequencies, and wherein computing the magnitudes comprises distinguishing among the components of the electrical signal by discriminating among the different frequencies.

10. The method according to claim 8, wherein estimating the position of the probe comprises refining the position of the probe by performing an iterative position estimation process that uses at least the lateral position as an initial condition.

11. The location pad arrangement according to claim 1,
wherein the location pad field generators comprise at least five coils;
wherein the control console comprises at least one of a memory media and a programmable digital hardware component;
wherein said memory media or programmable digital hardware component holds instructions for controlling the coils; and
wherein said instructions, when executed by the control console, cause the at least five coils of the location pad to each generate signals at different respective frequencies, the at least five coils each being driven by alternating current (AC) signals having different respective frequencies.

12. The location pad arrangement according to claim 1,
wherein the at least five field generators are positioned in a grid arrangement comprising a plurality of rows and a plurality of columns, wherein each row comprises a plurality of field generators, and wherein each column comprises a plurality of field generators.

13. The location pad arrangement according to claim 1,
wherein the location pad arrangement comprises a patient table and an MRI scanner;
wherein the location pad is located on a top surface of the patient table, and the patient table is shaped to support a human patient thereon;
wherein the patient table is movable into the MRI scanner; and
wherein the MRI scanner and the location pad are adapted for simultaneous operation.

14. The location pad arrangement according to claim 1,
wherein the position sensor of the body probe is a single axis sensor comprising a sensor coil.

15. The location pad arrangement according to claim 1,
wherein the body probe comprises a catheter, and the position sensor is located at a distal end of the catheter.

16. A location pad:
the location pad comprising a housing, the housing comprising at least one flat surface;
the location pad further comprising at least five field generators fixed to the housing, the at least five field generators being configured to generate respective magnetic fields having respective axes that are perpendicular to the flat surface of the location pad,
wherein the at least five field generators are arranged in two different dimensions with respect to the flat surface of the location pad such that the at least five field generators are not all arranged in a straight line;
wherein the location pad comprises a plurality of substantially rigid planar rows which are parallel to each other and which collectively form the flat surface;
wherein the at least five field generators are positioned on a plurality of different rows, with at least some rows each holding a plurality of field generators; and
wherein the plurality of different rows are capable of pivoting with respect to other adjacent rows such that the plurality of different rows of the location pad can collectively form a concave surface.

17. The location pad according to claim 16:
wherein each of the plurality of different rows is elongated and comprises a plurality of field generators, and;
wherein the plurality of field generators in each row are arranged in a line.

18. A location pad:
the location pad comprising a housing, the housing comprising at least one flat surface;
the location pad further comprising at least five field generators fixed to the housing, the at least five field generators being configured to generate respective magnetic fields having respective axes that are perpendicular to the flat surface of the location pad,
wherein the at least five field generators are arranged in two different dimensions with respect to the flat surface of the location pad such that the at least five field generators are not all arranged in a straight line;
wherein the location pad comprises a plurality of substantially rigid planar rows which collectively form the flat surface;
wherein the at least five field generators are positioned on the plurality of rows, with at least some of the plurality of rows each holding a plurality of field generators;
wherein the plurality of rows are capable of pivoting with respect to other adjacent rows such that the plurality of rows of the location pad can collectively form a concave surface; and
wherein a plurality of the at least five field generators are each individually surrounded by a respective concave trench, and wherein each trench is at least partially filled with elastic material, the elastic material therefore surrounding the respective field generators, and being adapted to dampen frequency resonances.

19. A location pad arrangement:
the location pad arrangement comprising a location pad according to claim 18, a body probe, and a control console.

20. A location pad arrangement:
the location pad arrangement comprising a location pad according to claim 18, a body probe, and a control console;
wherein the location pad arrangement comprises a patient table and an MRI scanner;
wherein the location pad is located on a top surface of the patient table, and the patient table is shaped to support a human patient thereon;
wherein the patient table is movable into the MRI scanner; and
wherein the MRI scanner and the location pad are adapted for simultaneous operation.

\* \* \* \* \*